(12) United States Patent
Beliakov et al.

(10) Patent No.: US 6,856,133 B1
(45) Date of Patent: Feb. 15, 2005

(54) METHOD AND APPARATUS FOR DETECTING A SUBSTANCE USING A NUCLEAR RESONANCE

(75) Inventors: Alexandre V Beliakov, Perth (AU); Taras N Rudakov, Perth (AU); Vassili T Mikhaltsevitch, Perth (AU); Warrick P Chisholm, Perth (AU)

(73) Assignee: Thorlock International Limited, Perth (AU)

( * ) Notice: Subject to any disclaimer, the term of this patent is extended or adjusted under 35 U.S.C. 154(b) by 0 days.

(21) Appl. No.: 10/110,099

(22) PCT Filed: Oct. 6, 2000

(86) PCT No.: PCT/AU00/01214

§ 371 (c)(1),
(2), (4) Date: Jul. 16, 2002

(87) PCT Pub. No.: WO01/25809

PCT Pub. Date: Apr. 12, 2001

(30) Foreign Application Priority Data

Oct. 6, 1999 (AU) .............................................. PQ3282

(51) Int. Cl.[7] .............................................. G01V 3/00
(52) U.S. Cl. ...................................... 324/307; 324/309
(58) Field of Search ................................. 324/307, 309, 324/300, 311, 318, 322, 313, 301

(56) References Cited

U.S. PATENT DOCUMENTS

| | | | | |
|---|---|---|---|---|
| 4,651,097 A | * | 3/1987 | Iwaoka et al. | 324/309 |
| 4,918,387 A | | 4/1990 | McKinnon et al. | 324/309 |
| 5,168,224 A | | 12/1992 | Maruizumi et al. | 324/307 |

(List continued on next page.)

FOREIGN PATENT DOCUMENTS

| | | | | |
|---|---|---|---|---|
| GB | 2 338 787 | 12/1999 | | |
| WO | WO 92/17794 | 10/1992 | ........... | G01R/33/44 |
| WO | WO 0092/17794 | * 10/1992 | ........... | G01R/33/44 |
| WO | WO 96/26543 A3 | 8/1996 | | |
| WO | WO 99/19740 | 4/1999 | | |

OTHER PUBLICATIONS

Carr, "Steady–State Free Precession in Nuclear Magnetic Resonance," *Physical Review*, vol. 112, No. 5, Dec. 1, 1958, pp. 1693–1701.

Ernst et al., "Application of Fourier Transform Spectroscopy to Magnetic Resonance," *Review of Scientific Instruments*, 1/66, 37(1): 93–102.

(List continued on next page.)

*Primary Examiner*—Brij B. Shrivastav
(74) *Attorney, Agent, or Firm*—Nixon & Vanderhye (57) ABSTRACT

A method and apparatus for detecting a prescribed substance in a specimen, using nuclear quadrupole resonance or nuclear magnetic resonance. The nuclei of the specimen are irradiated with a modified steady state free precession RF pulse sequence comprising a plurality of pulses. The pulse sequence includes pairs of pulses offset from each other by a prescribed phase shift to produce a plurality of nuclear resonance echo signals from the prescribed substance, if present. The pulse sequence is constructed with pairs of pulses where phases of adjacent pulse pairs are offset by 90° of the type: $[\tau/2-(\theta-\Delta\tau-\theta)_{0°}-\tau-(\theta-\Delta\tau-\theta)_{90°}-\tau/2]_n$, and where the transmit frequency has an offset relative to the resonant frequency of an irradiated nuclei of the prescribed substance. The echo signals are analyzed using Fourier transform and filtering techniques to register only those echo signals that are near the resonance frequencies of irradiated nuclei of the prescribed substance being detected. The registered echo signals are then compared with set reference values corresponding to the prescribed substance to determine whether the prescribed substance is present or not in the specimen. This type of detection method is not affected by temperature variations or other factors that create intensity anomalies. The pulse sequence creates additional echo signals, which increases the intensity of the observed signal and thus the signal to noise ratio. It also attenuates the effect of magneto-acoustic ringing.

30 Claims, 6 Drawing Sheets

U.S. PATENT DOCUMENTS

| | | | | |
|---|---|---|---|---|
| 5,233,300 A | | 8/1993 | Buess et al. | 324/309 |
| 5,365,171 A | | 11/1994 | Buess et al. | 324/307 |
| 5,457,385 A | * | 10/1995 | Sydney et al. | 324/301 |
| 5,491,414 A | | 2/1996 | Smith et al. | 324/309 |
| 5,592,083 A | | 1/1997 | Magnuson et al. | 324/307 |
| 6,127,824 A | | 10/2000 | Smith et al. | 324/307 |

OTHER PUBLICATIONS

Ernst et al., "The Dynamics of Nuclear Spin Systems," Chapter 2, of *Principles of Nuclear Magnetic Resonance in One and Two Dimensions*, Clarendon Press, Oxford, 1987, pp. 9–69.

Gerothanassis, "Methods of Avoiding the Effects of Acoustic Ringing in Pulsed Fourier Transform Nuclear Magnetic Resonance Spectroscopy," *Progress in NMR Spectroscopy*, vol. 19, 1987, pp. 267–329.

Hinshaw, "Image formation by nuclear magnetic resonance: The sensitive–point method," *Journal of Applied Physics*, vol. 47, No. 8, 8/76, pp. 3709–3721.

Kim et al., "Experimental Investigations of the Strong Off–Resonant Comb (SORC) Pulse Sequence in $^{14}$NQR," *Z. Naturforsch*, 47a, 1992, pp. 415–420.

Rudakov, "A low–frequency instrument for remote nuclear quadrupole resonance experiments," *Measurement Sci & Tech*, pp 444–448, 1997.

Rudakov, "The use of multi–pulse nuclear quadrupole resonance techniques for the detection of explosives containing RDX," *Journal of Applied Physics D: Applied Physics*, 30(9), pp. 1377–1382, 1997.

Rudakov, "Modifications of the steady–state free–precession sequence for the detection of pure nuclear quadrupole resonance," *Journal of Applied Physics D: Applied Physics*, 31:1251–1256, 1998.

* cited by examiner

Fig. 1

SSFP Sequence

METHOD AND APPARATUS FOR DETECTING A SUBSTANCE USING A NUCLEAR RESONANCE

CROSS-REFERENCE TO RELATED APPLICATION

The application is the national stage of PCT/AU00/01214, filed Oct. 6, 2000, which designated the United States.

FIELD OF THE INVENTION

The present invention relates to the practical use of nuclear resonance for material identification and more specifically to the use of nuclear quadrupole resonance (NQR) and nuclear magnetic resonance (NMR) in the detection of, amongst other things, explosive and narcotic substances.

Throughout the specification, unless the context requires otherwise, the word "comprise" or variations such as "comprises" or "comprising", will be understood to imply the inclusion of a stated integer or group of integers but not the exclusion of any other integer or group of integers.

BACKGROUND ART

It is described in the paper by Carr, "*Steady-State Free Precession in Nuclear Magnetic Resonance*", *Physical Review*, vol. 112, No. 5, 1958, pp. 1693–1701 that irradiation of a prescribed substance with so-called "Steady-State Free Precession" (SSFP) multi-pulse sequences, under certain conditions, produces an echo signal in the form of a non-decaying chain of signals from the prescribed substance. Consequently, such multi-pulse sequences have been used effectively in nuclear quadrupole resonance (NQR) for detecting explosive and narcotic substances, as described in SU Patent Specification No. 1,824,559 (Kuznetsov and Koblev), U.S. Pat. No. 5,365,171 (Buess et al), and in the paper by Rudakov and Belyakov, "*Modifications of the Steady-State Free Precession Sequence for the Detection of Pure Nuclear Quadrupole Resonance*", *Journal of Physics D: Applied Physics*, vol.31, 1998, 1251–1256.

However, the use of SSFP multi-pulse sequences is hampered by undesirable effects such as intensity anomalies. Intensity anomalies arise from the dependence of the observed signal amplitude of the echo signal on the offset from the NQR resonance frequency. This dependence is cyclic in nature, and the repetition period equals the inverse of the interval between pulses. intensity anomalies are undesirable and can arise in particular when detecting explosives and narcotics by NQR or NMR methods due to temperature variations and/or other factors such as temperature gradient (across the substance), crystalline impurities, crystalline phase and pressure.

The reason for this is that the nuclear quadrupole resonance frequency is dependent on the temperature of a substance, as well as these other factors, and hence the resonance frequency will drift with temperature. For example, trinitrotoluene (TNT) has a temperature dependence on resonance frequencies of NQR lines of more than 100 Hz/° K. and for cyclonite (RDX) it is more than 400 Hz/° K.

In view of the effect of intensity anomalies, very precise tuning of the transmit frequency in relation to the resonance frequency is required in order to obtain the maximum echo signal. Hence, although the value of the transmit frequency is the same, the intensity of the signal can vary according to the variations in temperature.

In the Kuznetsov and Koblev SU Patent No. 1,824,559, the following method of eliminating intensity anomalies is suggested. The prescribed substance is irradiated with a sequence of coherent pulses with a flip angle $\theta$ and a repetition period $\tau$, providing a basic sequence of the SSFP type:

$$[\tau/2-\theta-\tau/2]_n,$$

where n is the number of cycles (or alternatively: $[\theta-\tau]_n$).

The irradiation is carried out in series, with the carrier frequency of each sequence corresponding to one of the following values:

$$f_0 \text{ and } f_0 \pm \frac{2}{\tau},$$

$f_0$ being close to the resonance frequency of the substance being detected.

If no signal is observed when irradiating with a sequence with the carrier frequency $f_0$, then the sequence with the carrier frequency $$f_0 \pm \frac{2}{\tau}$$

is used.

The difference in these carrier frequencies corresponds to the difference between the frequency at which a maximum intensity signal is observed and the frequency at which a minimum intensity is observed. When the prescribed substance sought to be detected is not discovered in an examined specimen, the method is repeated with the time of observation increased twofold.

The Buess et al U.S. Pat. No. 5,365,171 describes the use of a combination of phase alternation pulse sequence (PAPS) and non-phase alternation pulse sequence (NPAPS) which permits irradiation of an examined specimen in which a prescribed substance is ought to be detected without switching the transmit frequency.

In this case, if a maximum signal is observed in the PAPS observation window, then a minimum signal will be observed in the NPAPS observation window.

Consequently, the total signal intensity is $\sqrt{2}$ times less than (or approximately 70% of) the maximum possible intensity achieved when using the sequence:

$$[\tau/2-\theta-\tau/2]_n.$$

In other words, an intrinsic limitation of this method is that it can only recover $1/\sqrt{2}$ or approximately 70% of the maximum available signal by virtue of the summation process of the two pulse amplitudes, whatever the pulse spacing.

Thus, the use of the above methods for reducing temperature variation or other effects that cause the intensity anomalies for a preset number of accumulations, is associated with a decrease in the net intensity of the echo signal as compared with the maximum observed when using a sequence of identical pulses of the type:

$$[\tau/2-\theta-\tau/2]_n.$$

A problem with the use of multi-pulse sequences in both NQR and NMR, however, is their connection with undesirable phenomena such as prove ringing (caused by transient processes in the resonance circuit) and magnetoacoustic ringing.

The duration of transient processes in probe ringing at NQR frequencies can reach hundreds of microseconds, as discussed in the paper by Rudakov and Mikhaltsevich, *Instruments and Experimental Techniques*, Vol. 38, No, 6, Part 1, 744–745, 1995, and the frequency and phase of oscillations are determined by the transmit frequency of RF pulses.

Magnetoacoustic ringing in NQR and NMR is created by ferromagnetic (metallic or ceramic) specimens, which can occur inside a specimen that is scanned for detecting the presence of a prescribed substance.

The nature of magnetoacoustic ringing in NQR and NMR is linked with re-orientation of magnetic domains in magnetised materials under the influence of a pulsed radio frequency magnetic field. The change in the orientation of domains occurs as periodical oscillations, the frequency of which coincides with the frequency of the RF pulses. The domain oscillations continue after the end of the RF pulse, gradually damping down due to dissipation forces inside the magnetic material and the loss of energy by electromagnetic re-emission. This re-emission can last for several milliseconds. The value of the signal induced by re-emission can be greater than the NQR signal from a prescribed substance. The frequency and phase of this signal depends only on the transmit frequency.

In the Buess et al U.S. Pat. No. 5,365,171, it is suggested to use the following method for the aforementioned combination of NPAPS and PAPS to eliminate probe ringing and magnetoacoustic ringing:

$$[\theta_{0°}-\tau-\theta_{0°}-\tau]_n[\theta_{0°}-\tau-\theta_{180°}-\tau]_{n'}.$$

As is stated in the Buess et al patent specification, the magnetoacoustic signal has the same phase as the initial RF pulse.

The NQR signal contains two components: free induction decay and echo, with the induction signal always being in phase with the RF pulse, and the echo signal being 180° out of phase to the induction signal when irradiated with NPAPS and in phase when irradiated with PAPS. The resulting signal presents a complex combination of induction signals, echo, probe ringing and magnetoacoustic ringing, which are then processed digitally. The signals received after the NPAPS $\theta_{180°}$ pulse and the two PAPS $\theta_{0°}$ pulses are added together and subtracted from the signal received after the NPAPS $\theta_{0°}$ pulse. The result is that both the induction and the ringing inputs are completely excluded from the total signal.

The disadvantage of this method is the further decrease of the intensity of the echo signal that occurs due to the exclusion of the induction signals. Furthermore, the pulse sequence:

$$[\theta_{0°}-\tau-\theta_{0°}-\tau]_n[\theta_{0°}-\tau-\theta_{180°}-\tau]_n,$$

is a combination of sequences of the SSFP type, with phase anomalies observed inside each sequence. Such phase anomalies are discussed in the book by Ernst, Bodenhausen and Wokaun, *Principles of Nuclear Magnetic Resonance In One and Two Dimensions*, Chap. 2, Clarendon Press, Oxford, 1987.

Thus the phase correlation between the induction signals and echo signals, established in the Buess et al U.S. Pat. No. 5,365,171, is only true for exact resonance, as well as for transmit frequencies offset from the resonance frequency by the value $\Delta f$ so that the relation $\Delta f\tau=m$ is true, where m is an integer. If the above phase correlations at $\Delta f\tau \neq m$ are not complied with, the signal is further decreased because the suggested scheme of accumulation ceases to be optimal.

With respect to the application of NMR to substance detection, intensity variation caused by drift and variation in the static magnetic field is also a problem, which is not overcome by use of any of the aforementioned pulse sequences.

SUMMARY OF THE INVENTION

It is an object of this invention to increase the accuracy of detection of prescribed substances such as, but not limited to, certain explosives and narcotics, in specimens, compared with previously known methods of detecting same using nuclear resonance such as NQR or NMR.

It is a preferred object of the present invention to overcome interference from probe ringing and magnetoacoustic ringing to enable the accurate detection of prescribed substances such as, but not limited to, certain explosives and narcotics, in a specimen using nuclear resonance.

It is a further, or alternative, preferred object of the present invention to substantially overcome or accommodate the temperature effects or the effects of other intensity varying mechanisms arising from detecting substances using multi-pulse NQR or NMR.

These and other objects of the invention are accomplished by the use of a pulse sequence comprising a plurality of pulses which irradiate the nuclei of a specimen in which a prescribed substance is sought to be detected, to produce a plurality of nuclear resonance echo signals in the prescribed substance if present that can be detected and analysed.

Thus, in accordance with one aspect of the present invention, there is provided a method for detecting a prescribed substance in a specimen, comprising:

irradiating the nuclei of a specimen in which a prescribed substance is sought to be detected, with a pulse sequence comprising a plurality of pulses, wherein the pulse sequence includes pairs of pulses offset from each other by a prescribed phase shift to produce a plurality of nuclear resonance echo signals from the prescribed substance, if present; and analysing the echo signals to detect the presence of the prescribed substance.

By using a pulse sequence that produces a plurality of nuclear resonance echo signals, as opposed to a single nuclear resonance echo signal that arises from using either the PAPS/NPAPS combination or the basic SSFP pulse sequence, a higher signal to noise ratio can be achieved with the produced nuclear resonance signals, enabling the echo signals to be analysed to detect the presence of a prescribed substance in the specimen, irrespective of the effect of temperature and other factors on the intensity of the nuclear resonance echo signals.

Preferably, the pulse sequence is constructed with pairs of pulses with phases of adjacent pulse pairs offset by 90° of the type:

$$[\tau/2-(\theta-\Delta\tau-\theta)_{0°}-\tau-(\theta-\Delta\tau-\theta)_{90°}-\tau/2]_n,$$

and the transmit frequency having an offset relative to the resonant frequency of an irradiated nuclei of the prescribed substance.

In accordance with another aspect of the present invention, there is provided a method for detecting the presence of a prescribed substance in a specimen comprising:

transmitting a multi-pulse sequence at a transmit frequency to irradiate nuclei in a specimen therewith, within a set temperature range;

receiving and analysing nuclear resonance echo signals issued by any resonant nuclei within said specimen irradiated by said multi-pulse sequence to detect the presence of the prescribed substance in the specimen; and wherein said multi-pulse sequence comprises paired pulses with phases of adjacent pulse pairs offset by 90° of the type:

$$[\tau/2-(\theta-\Delta\tau-\theta)_{0°}-\tau-(\theta-\Delta\tau-\theta)_{90°}-\tau/2]_n;$$

said transmit frequency has an offset in relation to the predetermined resonance frequency of irradiated nuclei of the prescribed substance; and said analysing involves performing a Fourier transform on the received nuclear resonance echo signals, registering only those echo signals falling within a narrow band range corresponding to the resonance frequencies of irradiated nuclei of said prescribed substance in the set temperature range, and then comparing the registered echo signals with set reference values corresponding to said prescribed substance to determine whether said prescribed substance is present or not in said specimen.

In this manner, the paired pulses of the multi-pulse signal create additional echo signals in observation windows of the sequence, which increases the intensity of the received signal.

Preferably, the method includes receiving said nuclear resonance echo signals in all observation windows of a multi-pulse sequence, corresponding to time intervals between adjacent pulse pairs, and said analysing includes summing said time intervals in each window to obtain a resultant signal and subjecting said resultant signal to said Fourier transform.

In this manner, the Fourier transform distinguishes the nuclear resonance echo signal issued by any prescribed substance present in said specimen from probe and acoustic ringing by differences in frequency.

In accordance with a further, but not necessarily essential, aspect of the invention, there is provided a method for detecting a substance within a class of explosives and narcotics, such as those that may contain a $^{14}$N, $^{35}$Cl, $^{39}$K or $^{37}$Cl nucleus in a specimen, the method employing nuclear quadrupole resonance and comprising the steps of:

(a) generating a modified steady state free precession RF pulse sequence, said RF pulse sequence consisting of paired pulses, each paired pulse of said RF sequence being of the same duration, paired pulse separation and predetermined frequency, and the phase of each even paired pulse of said RF pulse sequence being shifted 90° with respect to each odd paired pulse of said RF pulse sequence, wherein each pulse of said paired pulse is of the same phase, duration and pulse separation inside said paired pulse;

(b) transmitting said RF pulse sequence to a probe;

(c) irradiating the specimen with said RF pulse sequence transmitted to said probe at said step (b);

(d) detecting nuclear quadrupole resonance echo signals between paired pulses of said RF pulse sequence transmitted to said probe in response to irradiating the specimen at said step (c);

(e) summing all said nuclear quadrupole resonance echo signals to generate a resultant signal;

(f) subjecting said resultant signal to a Fourier transform;

(g) generating a Fourier transformed signal as a result of said Fourier transform;

(h) frequency filtering said Fourier transformed signal;

(i) comparing a signal obtained after filtering at said step (h) to a predetermined reference magnitude; and (j) signalling when said filtered signal exceeds said predetermined reference magnitude.

Preferably, said pulse separation inside said paired pulses is much less than said paired pulse separation between neighbouring said paired pulses.

Preferably, the lowest frequency of said filtered signal is about 0.5–1.0 kHz.

Preferably, said predetermined frequency of said RF pulse sequence is set near to a nuclear quadrupole resonance frequency of a quadrupolar nucleus such as $^{14}$N, $^{35}$Cl, $^{39}$K or $^{37}$Cl in said substance to be detected.

Preferably, said substance to be detected comprises an explosive or narcotic including a $^{14}$N nucleus.

Preferably, said substance to be detected comprises an explosive or narcotic including a $^{35}$Cl nucleus.

Preferably, said substance to be detected comprises an explosive or narcotic including a $^{37}$Cl nucleus.

Preferably, said substance to be detected comprises an explosive or narcotic including a $^{39}$K nucleus.

In accordance with another aspect of the present invention, there is provided an apparatus for detecting the presence of a prescribed substance in a specimen comprising:

generating means to generate a pulse sequence comprising a plurality of pulses, wherein the pulse sequence includes pairs of pulses offset from each other by a prescribed phase shift;

irradiating means to irradiate the nuclei of a specimen in which the presence of a prescribed substance is sought to be detected, with said pulse sequence; and analysing means to analyse any echo signals produced in the specimen on irradiating same with said pulse sequence to detect the presence of the prescribed substance;

wherein the pulse sequence is of type that is capable of producing a plurality of nuclear resonance echo signals from the prescribed substance, if present in the specimen.

In accordance with another aspect of the present invention, there is provided an apparatus for detecting the presence of a prescribed substance in a specimen comprising:

multi-pulse sequence generating means to generate a multi-pulse sequence comprising paired pulses with phases of adjacent pulse pairs offset by 90° of the type:

$$[\tau/2-(\theta-\Delta\tau-\theta)_{0°}-\tau-(\theta-\Delta\tau-\theta)_{90°}-\tau/2]_n;$$

transmitting means to transmit said multi-pulse sequence at a transmit frequency offset in relation to the predetermined resonant frequency of irradiated nuclei of a prescribed substance to permeate a specimen and accommodate any intensity variation mechanisms;

receiving means to receive nuclear resonance echo signals issued by any nuclei within said specimen irradiated by said multi-pulse sequence;

analysing means to analyse said received resonance echo signals and establish whether any of received resonance echo signals indicate the presence of said prescribed substance in said specimen; and alarm means to issue an alarm in response to said analysing means establishing that some of said received nuclear resonance echo signals indicate the presence of said prescribed substance in said specimen;

wherein said analysing involves summing all said nuclear resonance echo signals to generate a resultant signal, performing a Fourier transform on said resultant resonance signal, registering only those signals falling within a narrow band range corresponding to the resonance frequencies of irradiated nuclei of said prescribed substance in the set temperature range, and then comparing the registered signals with said set reference values corresponding to said prescribed substance to determine whether said prescribed substance is present or not in said specimen.

This approach increases the signal-to-noise ratio by approximately $\sqrt{2}$ times in comparison to previously mentioned prior art techniques, and in practice excludes intensity variations due to temperature changes and other intensity variation mechanisms.

BRIEF DESCRIPTION OF THE DRAWINGS

The invention will be better understood in the light of the following description of one preferred embodiment thereof. The description is made with reference to the accompanying drawings, wherein.

DESCRIPTION OF THE PREFERRED EMBODIMENT

The embodiment is directed towards a device and method using NQR for detecting the presence of quadrupolar substances, which exhibit NQR intensity variations resulting from temperature variation and other factors such as temperature gradient (across the substance), crystalline impurities, crystalline phase and pressure. Such materials include certain types of explosives and narcotics substances containing quadrupolar nuclei such as $^{14}N$, $^{35}Cl$, $^{39}K$ or $^{37}Cl$. Specific examples would be RDX ($C_3H_6N_6O_6$) and cocaine ($C_{17}H_{21}NO_4$).

Figure 1:
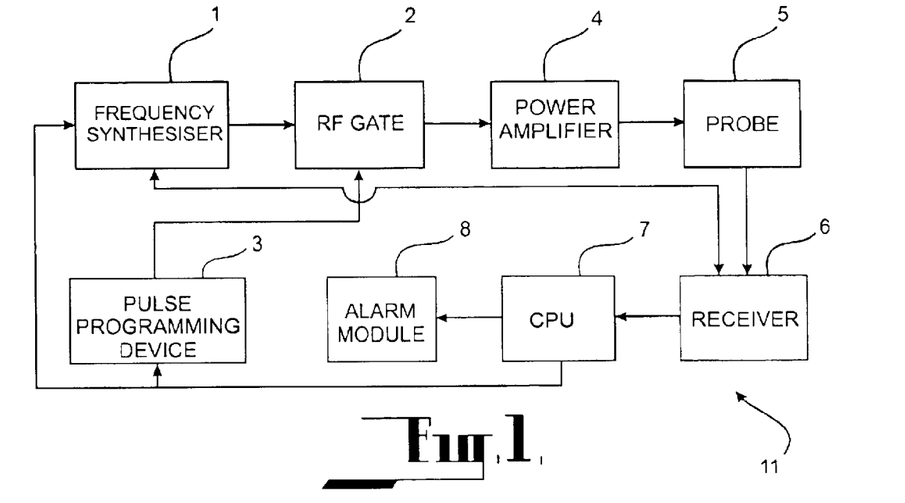
FIG. 1 shows a block diagram for the present invention embodied in the form of an NQR system.

As shown in FIG. 1, in general terms, a device 11 for detecting the explosive or narcotic substance includes a frequency synthesiser (FS) 1 which generates an oscillating signal with a frequency $f_0$ close to the NQR frequency of the prescribed substance sought to be detected. The oscillating signal is then passed to the input of a radio frequency (RF) gate 2, which is controlled by a signal from a pulse programming device 3, to generate a programmed RF pulse sequence at the output of the RF gate 2. The RF pulse sequence is then amplified via a power amplifier 4 and is then passed to a transmit and receive probe 5 disposed adjacent to a specimen being examined by the device.

The probe 5 includes an induction coil, which forms part of a resonance circuit, so that a radio frequency magnetic field is created in the examined volume of the specimen, on the amplified RF pulse sequence being passed through the probe. The induction coil of the probe 5 is disposed so as to be coupled with the RF magnetic field created in the specimen and receives any NQR echo signal generated by the prescribed substance sought to be detected, if it is present in the examined volume of the specimen.

The received NQR echo signal is conveyed to a receiver 6, which amplifies the received signal and performs quadrature detection. Accordingly, the receiver 6 includes digital filtering means to filter the received echo signal. For this purpose reference voltages are conveyed to the receiver 6 from the frequency synthesiser 1, with the phase of one signal shifted by 90° in relation to the phase of the other signal. Low-frequency signals from the output of the quadrature channels are conducted to a central processing unit (CPU) 7, which performs analogue-to-digital conversion, coherent accumulation, a Fourier transform of the signals and frequency filtering.

The CPU 7 also controls the frequency of the oscillating signal output from the FS 1, and the signal output from the pulse programming device 3 which controls the switching of the RF gate 2.

After the pulse sequence has been applied to the specimen, the CPU 7 extracts the NQR echo signal in the preset frequency range proximate to the NQR frequency of the substance sought to be detected, and compares the magnitude of the extracted signal with a predetermined threshold magnitude corresponding to that which would be expected if a requisite amount of the substance being sought to be detected, was actually present. This threshold magnitude is set, taking into account the relative probability of detection and false alarm rates.

When the predetermined threshold magnitude is exceeded, the CPU 7 activates an alarm signal, which is conveyed to an alarm module 8.

When searching for several types of explosives and narcotics substances, the above procedure is repeated for each substance sought to be detected, with the FS 1 and probe circuit 5 being re-tuned to the frequency, corresponding to the resonance frequency of the substance sought to be detected.

Now describing the methodology associated with the preferred embodiment of the present invention in more detail, the pulse sequence applied to the probe uses a modified version of the SSFP sequence, described by the formula:

$$[\tau/2-(\theta-\Delta\tau-\theta)_{0°}-\tau-(\theta-\Delta\tau-\theta)_{90°}-\tau/2]_n,$$

where $\theta$ is a flipping angle, $\tau$ is the interval between pairs of pulses, $\Delta\tau$ is the interval between the pulses within the pair, with $\Delta\tau$ being considerably less then $\tau$, and the lower indices 0° and 90° show the phase of the transmit pulse frequency.

Figure 2:
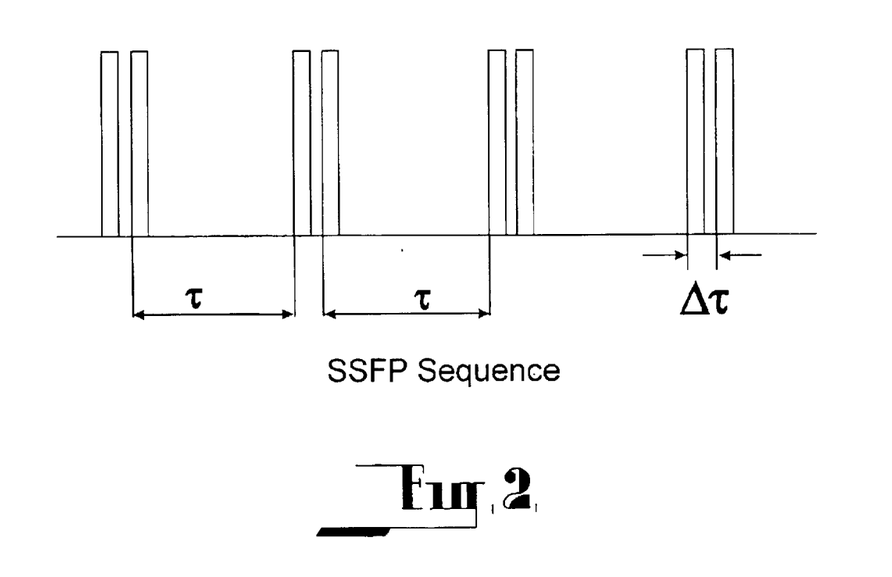
FIG. 2 shows a timing diagram of the modified version of the SSFP sequence of the type: $[\tau/2-(\theta-\Delta\tau-\theta)_{0°}-\tau-(\theta-\Delta\tau-\theta)_{90°}-\tau/2]_n$.

As mentioned, FIG. 2 is a timing diagram of the version of the particular SSFP sequence which is adopted in the present embodiment. Although FIG. 2 shows rectangular shaped pulses, any other pulse shape can be used.

Figure 3A:
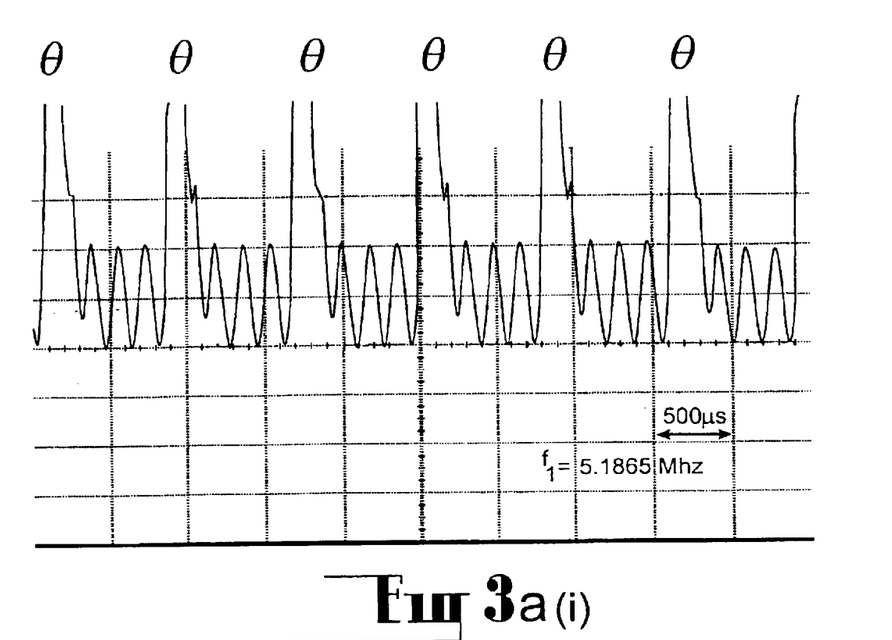
FIG. 3a, 3b and 3c show the picture of the echo signal in the time domain, received using the sequences NPAPS, PAPS and of the modified version of the SSFP sequence of the type which is the subject of the present invention, respectively, for two discrete transient frequencies.
Figure 3B:
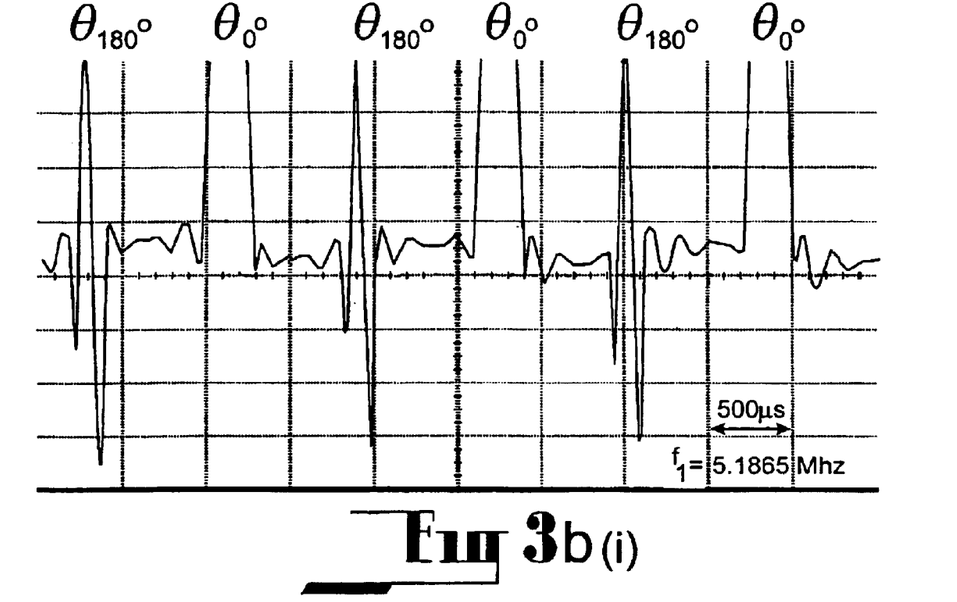
Figure 3C:
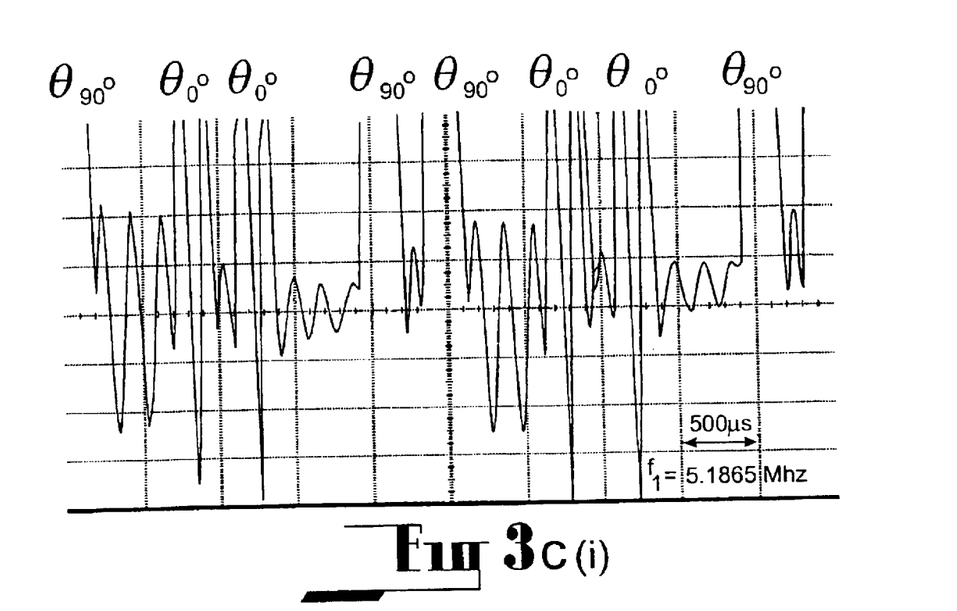

FIG. 3a, 3b and 3c show the trace of the NQR echo signals received, in the time domain, using the sequences NPAPS, PAPS and $[\tau/2-(\theta-\Delta\tau-\theta)_{0°}-\tau-(\theta-\Delta\tau-\theta)_{90°}-\tau/2]_n$ respectively, for two values of the transmit frequency, where the subfigures (i) use the transmit frequency $f_1=5.1865$ MHz and the subfigures (ii) use the transmit frequency $f_2=5.1871$ MHz. These two transmit frequencies respectively correspond to the maximum and minimum of the signal intensity when using NPAPS.

Experimental data obtained for RDX using the device 11 at a temperature of 23° C. resulted in sequences being used with the following parameters: $\theta=30°$, $\tau=0.8$ ms, $\Delta\tau=0.2$ ms, $n=50$.

The use of paired pulses creates additional echo signals in the observation windows of the sequence, which increases the intensity of the NQR signal. For the example, as shown in FIG. 3c, the maximum intensity of the signal and signal-to-noise ratio increases by 30% as compared with similar values when any other sequence, PAPS, NPAPS or $[\tau/2-\theta-\tau/2]_m$ is used.

It should be noted that when $m=2n$ the last sequence becomes equivalent to the NPAPS sequence.

FIG. 3 particularly demonstrates the improvement in the signal-to-noise ratio that is achieved when using the combination:

$$[\tau/2-(\theta-\Delta\tau-\theta)_{0°}-\tau-(\theta-\Delta\tau-\theta)_{90°}-\tau/2]_n,$$

as compared with the combination of PAPS and NPAPS. Changing the offset from frequency $f_1$ to frequency $f_2$, which can be caused by temperature effects, can cause $f_2$ to correspond to the maximum variation of the signal intensity in the windows of compared sequences.

When irradiating RDX with a combination of PAPS and NPAPS at frequency $f_1$, maximum intensity is achieved only in NPAPS windows. The intensity of the NQR signals in PAPS windows is minimal in this case and is less than 40% of the maximum (FIGS. 3a and 3b). Therefore the total value of the resultant signal after accumulation from 2n windows of the PAPS and NPAPS combination equals $1.4\,nU_{max}$, where $U_{max}$ is the signal amplitude in the NPAPS window.

The value of noise after 2n accumulations equals:

$$\sqrt{2n}\,U_n$$

($U_n$ is the amplitude of noise).

Consequently, signal-to-noise ratio approximately equals:

$$\sqrt{n}\left(\frac{U_{max}}{U_n}\right).$$

The same signal-to-noise ratio can be achieved when irradiating by the combination of the PAPS and NPAPS at a frequency $f_2$, which corresponds to the maximum signal in the NPAPS observation windows.

Now regard will be made to the operation of the embodiment when using the pulse sequence:

$$[\tau/2-(\theta-\Delta\tau-\theta)_{0°}-\tau-(\theta-\Delta\tau-\theta)_{90°}-\tau/2]_n,$$

at either frequency $f_1$ or $f_2$, as shown in FIG. 3c.

In this case, in every second window of the sequence (for example all the even windows), a maximum signal is observed, and in the other windows (odd windows) a minimum signal is observed. The value of the maximum signal equals $1.3\,U_{max}$ and the value of the minimum signal equals $0.7\,U_{max}$ (the value of $U_{max}$ is as defined earlier).

The noise value is similar to that of the previous example. The signal-to-noise ratio obtained as a result of accumulations from 2n windows equals:

$$\sqrt{2n}\left(\frac{U_{max}}{U_n}\right).$$

Consequently, the use of the given sequence increases the signal-noise ratio, characterising the sensitivity of the method, by $\sqrt{2}$ times as compared with the PAPS and NPAPS combination.

Figure 4A:
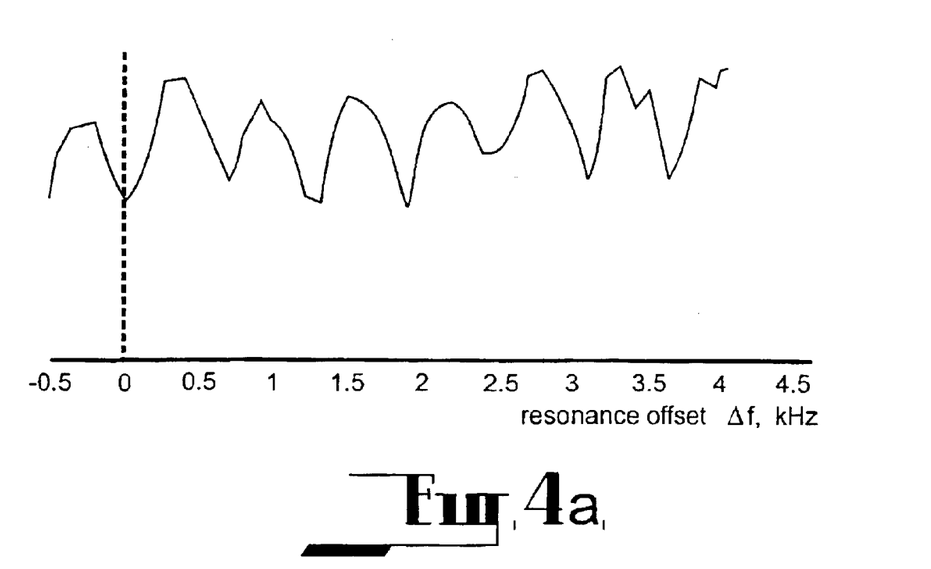
FIGS. 4a and 4b demonstrate the nature of the resultant signal with respect to frequency, obtained after summing of the received echo signals with frequency offsets corresponding to the multi-pulse sequences of the type: $[\theta_{0°}-\tau-\theta_{0°}-\tau]_n$, $[\theta_{0°}-\tau-\theta_{180°}-\tau]_n$; and $[\tau/2-(\theta-\Delta\tau-\theta)_{0°}-\tau-(\theta-\Delta\tau-\theta)_{90°}-\tau/2]_n$, respectively.
Figure 4B:
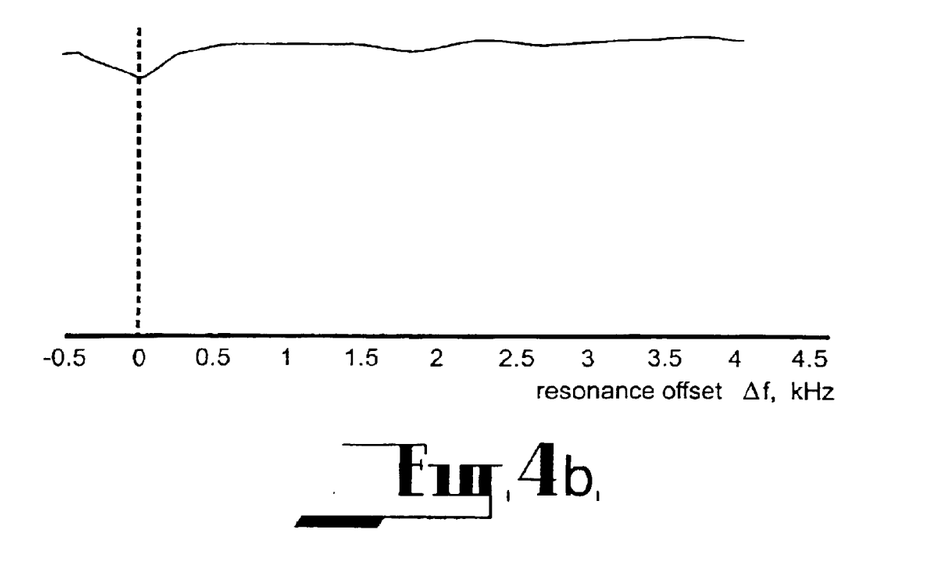

FIGS. 4a and 4b demonstrate the dependence of the resultant signal with respect to frequency, after the adding up of all windows of the sequence from the frequency offset of the sequences:

(i) $[\theta_{0°}-\tau-\theta_{0°}-\tau]_n[\theta_{0°}-\tau-\theta_{180°}-\tau]_n$ (the PAPS and NPAPS sequence); and (ii) $[\tau/2-(\theta-\Delta\tau-\theta)_{0°}-\tau-(\theta-\Delta\tau-\theta)_{90°}-\tau/2]_n$ (the sequence used in the preferred embodiment); respectively.

As can be seen, the use of the sequence:

$$[\tau/2-(\theta-\Delta\tau-\theta)_{0°}-\tau-(\theta-\Delta\tau-\theta)_{90°}-\tau/2]_n,$$

in contrast to the combination of the PAPS and NPAPS, completely excludes intensity variations, attributable to temperature or other variations, with the period $1/\tau$.

It should be appreciated that the use of a modified SSFP sequence with paired pulses, in accordance with the present embodiment, in conjunction with the analysing method which includes:

adding up signals of all windows of the sequence in one window,

Fourier transformation of the resultant summed signal, and digital filtration of the Fourier transformed signal which discriminates the sample signal from other components;

also allows cancellation of both probe ringing and magneto-acoustical ringing.

Moreover, the frequency of the probe ringing and magneto-acoustical ringing coincides with the transmit frequency of RF pulses of the multi-pulse sequence. The optimum offset of the transmit frequency of the sequence pulses:

$$[\tau/2-(\theta-\Delta\tau-\theta)_{0°}-\tau-(\theta-\Delta\tau-\theta)_{90°}-\tau/2]_n,$$

is several kHz relative to the resonance frequency. Therefore, the NQR echo signal and ringing after the Fourier transformation of the resultant signal are separated in the frequency domain by the offset value. Thus the use of the digital filtering means with a frequency bandwidth that is higher than the frequencies of the components of the ringing spectrum, allows exclusion of the ringing from the signal.

Figure 5:
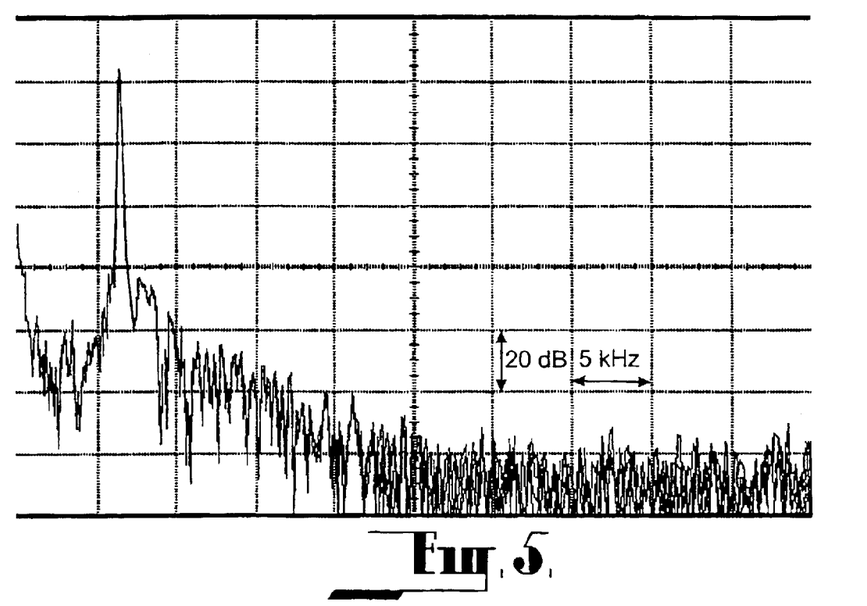
FIG. 5 shows the Fourier-spectrum of the Fourier transformed signal obtained for received NQR echo signals excited by the sequence $[\tau/2-(\theta-\Delta\tau-\theta)_{0°}-\tau-(\theta-\Delta\tau-\theta)_{90°}-\tau/2]_n$.

FIG. 5 shows the Fourier-spectrum of the Fourier transformed signal received from the NQR echo signal, excited by the sequence:

$$[\tau/2-(\theta-\Delta\tau-\theta)_{0°}-\tau-(\theta-\Delta\tau-\theta)_{90°}-\tau/2]_n,$$

and obtained after adding up all signals from the observation windows. In the present instance, the echo signal used was received from detection of the substance RDX at a transmit frequency 5.1865 MHz and a temperature of 23°. The parameters of the sequence coincide with those observed for the received echo signal presented in FIG. 3c(i). Peaks of the ringing signals correspond to zero frequency of the Fourier transformed signal, and the peak of the NQR echo signal is shifted by the offset frequency of 6.5 kHz.

Figure 6:
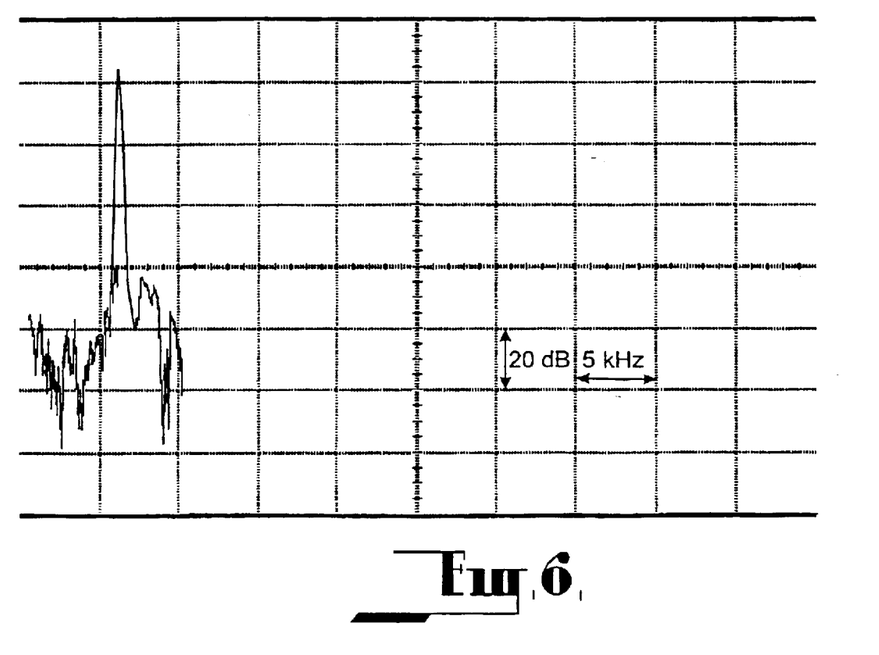
FIG. 6 demonstrates the Fourier-spectrum of the Fourier transformed signal obtained for received NQR echo signals corresponding to the signal in FIG. 5 falling within the narrow band of the resonance frequency of the prescribed substance, after digital filtering.

FIG. 6 shows the Fourier-spectrum of the obtained Fourier transformed signal shown in FIG. 5 after digital filtering.

The lower cut-off frequency of the filter equals 500 Hz. The spectrum in FIG. 6 shows the Fourier transformed signal for only the NQR echo signal, with ringing completely cancelled. The discriminated NQR echo signal is then compared with the reference value for RDX at a temperature of 23° C., which is preset according to the required true/false detection probability ratio.

The success of this embodiment using the given sequence arises from the following:

(a) When the transmit frequency offset from the resonance frequency is changed uncontrollably by temperature effects and other intensity variation mechanisms, the decrease in the intensity of the registered signal in some observation windows is compensated for by the increase of the intensity of the signal in the other windows.

(b) As the total signal is processed, which is obtained after accumulating all of the signals of the windows in the sequence, variations in intensity arising in a single window do not affect the net result.

(c) The use of paired pulses create additional echo signals in the observation windows, which increases the intensity of the observed signal and the signal-to-noise ratio, which in turn determines the sensitivity of the detection method.

A particular advantage of the present embodiment is that it attenuates the effect of magneto-acoustic ringing, which is normally produced by metal and other certain materials within the RF field. The invention achieves this by basically recognising the difference in decay time between magneto-acoustic interference and the NQR echo signal. Moreover, the NQR echo signal derived from the incident RF pulse sequence arrives after the magneto-acoustic signal has completely dissipated, thereby permitting NQR detection in the absence of magneto-acoustic interference.

It should be appreciated that the scope of the present invention is not limited to the particular embodiment described herein. In particular, the invention is not limited to the use of nuclear quadrupole resonance detecting techniques, but is also applicable to the use of nuclear magnetic resonance detecting techniques. In this respect, NMR is not limited to those substances containing quadrupolar nuclei, however, the invention is nonetheless applicable to all NMR materials. Further, the invention is not limited to the detection of substances including N and Cl quadrupolar nuclei, but may be equally applicable to the detection of substances containing other particular quadrupolar nuclei.

We claim:

1. A method for detecting a prescribed substance in a specimen, comprising:

irradiating the nuclei of a specimen in which a prescribed substance is sought to be detected, with a pulse sequence comprising a plurality of pulses, wherein the pulse sequence includes pairs of pulses offset from each other by a prescribed phase shift to produce a plurality of nuclear resonance echo signals from the prescribed substance, if present; and analysing the echo signals to detect the presence of the prescribed substance, wherein the pulse sequence is a modified steady state free precession pulse sequence comprising paired pulses, each paired pulse of said pulse sequence being of the same duration, paired pulse separation and predetermined frequency, and the phase of each even paired pulse of said pulse sequence being shifted 90° with respect to each odd paired pulse of said pulse sequence, and wherein each pulse of said paired pulse is of the same phase, duration and pulse separation inside said paired pulse.

2. A method as claimed in claim 1, wherein said pulse separation inside said paired pulses is much less than said paired pulse separation between neighbouring said paired pulses.

3. A method as claimed in claim 1, wherein the pulse sequence is constructed with pairs of pulses with phases of adjacent pulse pairs offset by 90° of the type:

$$[\tau/2-(\theta-\Delta\tau-\theta)_{0°}-\tau-(\theta-\Delta\tau-\theta)_{90°}-\tau/2]_n,$$

and the transmit frequency having an offset relative to the resonant frequency of an irradiated nuclei of the prescribed substance.

4. A method as claimed in claim 1, wherein said pulse sequence is a radio frequency (RF) pulse sequence.

5. A method for detecting the presence of a prescribed substance in a specimen comprising:

transmitting a multi-pulse sequence at a transmit frequency to irradiate nuclei in a specimen therewith, within a set temperature range;

receiving and analysing nuclear resonance echo signals issued by any resonant nuclei within said specimen irradiated by said multi-pulse sequence to detect the presence of the prescribed substance in the specimen;

said multi-pulse sequence comprising paired pulses with phases of adjacent pulse pairs offset by 90° of the type:

$$[\tau/2-(\theta-\Delta\tau-\theta)_{0°}-\tau-(\theta-\Delta\tau-\theta)_{90°}-\tau/2]_n;$$

said transmit frequency having an offset in relation to the predetermined resonance frequency of irradiated nuclei of the prescribed substance; and said analysing involves performing a Fourier transform on the received nuclear resonance echo signals, registering only those echo signals falling within a narrow band range corresponding to the resonance frequencies of irradiated nuclei of said prescribed substance in the set temperature range, and then comparing the registered echo signals with set reference values corresponding to said prescribed substance to determine whether said prescribed substance is present or not in said specimen.

6. A method as claimed in claim 5, including receiving said nuclear resonance echo signals in all observation windows of a multi-pulse sequence, corresponding to time intervals between adjacent pulse pairs, and said analysing includes summing said time intervals in each window to obtain a resultant signal and subjecting said resultant signal to said Fourier transform to distinguish the nuclear resonance echo signal issued by any prescribed substance present in said specimen from probe and acoustic ringing by differences in frequency.

7. A method as claimed in claim 5, wherein said pulse separation inside said paired pulses is much less than said paired pulse separation between neighbouring said paired pulses.

8. A method for detecting a substance within a class of explosives and narcotics, such as those that may contain a $^{14}N$, $^{35}Cl$, $^{39}K$ or $^{37}Cl$ nucleus in a specimen, the method employing nuclear quadrupole resonance and comprising the steps of:

(a) generating a modified steady state free precession RF pulse sequence, said RF pulse sequence comprising paired pulses, each paired pulse of said RF sequence being of the same duration, paired pulse separation and predetermined frequency, and the phase of each even paired pulse of said RF pulse sequence being shifted 90° with respect to each odd paired pulse of said RF pulse sequence, wherein each pulse of said paired pulse is of the same phase, duration and pulse separation inside said paired pulse;

(b) transmitting said RF pulse sequence to a probe;

(c) irradiating the specimen with said RF pulse sequence transmitted to said probe at said step (b);

(d) detecting nuclear quadrupole resonance echo signals between paired pulses of said RF pulse sequence transmitted to said probe in response to irradiating the specimen at said step (c);

(e) summing all said nuclear quadrupole resonance echo signals to generate a resultant signal;

(f) subjecting said resultant signal to a Fourier transform;

(g) generating a Fourier transformed signal as a result of said Fourier transform;

(h) frequency filtering said Fourier transformed signal;

(i) comparing a signal obtained after filtering at said step (h) to a predetermined reference magnitude; and (j) signalling when said filtered signal exceeds said predetermined reference magnitude.

9. A method as claimed in claim 8, wherein said pulse separation inside said paired pulses is much less than said paired pulse separation between neighbouring said paired pulses.

10. A method as claimed in claim 8, wherein the lowest frequency of said filtered signal is about 0.5–1.0 kHz.

11. A method as claimed in claim 8, wherein said predetermined frequency of said RF pulse sequence is set near to a nuclear quadrupole resonance frequency of a quadrupolar nucleus, such as $^{14}$N, $^{35}$Cl, $^{39}$K or $^{37}$Cl, in said substance to be detected.

12. A method as claimed in claim 8, wherein said substance to be detected comprises an explosive or a narcotic including a $^{14}$N nucleus.

13. A method as claimed in claim 8, wherein said substance to be detected comprises an explosive or narcotic including a $^{35}$Cl nucleus.

14. A method as claimed in claim 8, wherein said substance to be detected comprises an explosive or narcotic including a $^{37}$Cl nucleus.

15. A method as claimed in claim 8, wherein said substance to be detected comprises an explosive or narcotic including a $^{39}$K nucleus.

16. An apparatus for detecting the presence of a prescribed substance in a specimen comprising:

a pulse generator to generate a pulse sequence comprising a plurality of pulses, wherein the pulse sequence includes pairs of pulses offset from each other by a prescribed phase shift;

an irradiater to irradiate the nuclei of a specimen in which the presence of a prescribed substance is sought to be detected, with said pulse sequence; and an analyser to analyse any echo signals produced in the specimen on irradiating same with said pulse sequence to detect the presence of the prescribed substance;

wherein the pulse sequence is a modified steady state free precession pulse sequence comprising paired pulses, each paired pulse of said pulse sequence being of the same duration, paired pulse separation and predetermined frequency, and the phase of each even paired pulse of said pulse sequence being shifted 90° with respect to each odd paired pulse of said pulse sequence, and wherein each pulse of said paired pulse is of the same phase, duration and pulse separation inside said paired pulse, said pulse sequence being capable of producing a plurality of nuclear resonance echo signals from the prescribed substance, if present in the specimen.

17. An apparatus as claimed in claim 16, wherein said pulse separation inside said paired pulses is much less than said paired pulse separation between neighbouring said paired pulses.

18. An apparatus as claimed in claim 16, wherein the pulse sequence is constructed with pairs of pulses with phases of adjacent pulse pairs offset by 90° of the type:

$$[\tau/2-(\theta-\Delta\tau-\theta)_{0°}-\tau-(\theta-\Delta\tau-\theta)_{90°}-\tau/2]_n,$$

and the transmit frequency having an offset relative to the resonant frequency of an irradiated nuclei of the prescribed substance.

19. An apparatus as claimed in claim 16, wherein said pulse sequence is a radio frequency (RF) pulse sequence.

20. An apparatus for detecting the presence of a prescribed substance in a specimen comprising:

a multi-pulse sequence generator to generate a multi-pulse sequence comprising paired pulses with phases of adjacent pulse pairs offset by 90° of the type:

$$[\tau/2-(\theta-\Delta\tau-\theta)_{0°}-\tau-(\theta-\Delta\tau-\theta)_{90°}-\tau/2]_n;$$

a transmitter to transmit said multi-pulse sequence at a transmit frequency offset in relation to the predetermined resonant frequency of irradiated nuclei of a prescribed substance to permeate a specimen and accommodate any intensity variation mechanisms;

a receiver to receive nuclear resonance echo signals issued by any nuclei within said specimen irradiated by said multi-pulse sequence;

an analyser to analyse said received resonance echo signals and establish whether any of received resonance echo signals indicate the presence of said prescribed substance in said specimen; and an alarm to issue an alarm in response to said analysing means establishing that some of said received nuclear resonance echo signals indicate the presence of said prescribed substance in said specimen;

wherein said analysing involves summing all said nuclear resonance echo signals to generate a resultant signal, performing a Fourier transform on said resultant resonance signal, registering only those signals falling within a narrow band range corresponding to the resonance frequencies of irradiated nuclei of said prescribed substance in a set temperature range, and then comparing the registered signals with said set reference values corresponding to said prescribed substance to determine whether said prescribed substance is present or not in said specimen.

21. An apparatus for detecting the presence of a prescribed substance in a specimen comprising:

means for generating a pulse sequence comprising a plurality of pulses, wherein the pulse sequence includes pairs of pulses offset from each other by a prescribed phase shift;

means for irradiating the nuclei of a specimen in which the presence of a prescribed substance is sought to be detected, with said pulse sequence; and means for analysing any echo signals produced in the specimen on irradiating same with said pulse sequence to detect the presence of the prescribed substance;

wherein the pulse sequence is a modified steady state free precession pulse sequence comprising paired pulses, each paired pulse of said pulse sequence being of the same duration, paired pulse separation and predetermined frequency, and the phase of each even paired pulse of said pulse sequence being shifted 90° with respect to each odd paired pulse of said pulse sequence, and wherein each pulse of said paired pulse is of the same phase, duration and pulse separation inside said paired pulse, said pulse sequence being capable of producing a plurality of nuclear resonance echo signals from the prescribed substance, if present in the specimen.

22. An apparatus for detecting the presence of a prescribed substance in a specimen comprising:

means for generating a multi-pulse sequence comprising paired pulses with phases of adjacent pulse pairs offset by 90° of the type:

$$[\tau/2-(\theta-\Delta\tau-\theta)_{0°}-\tau-(\theta-\Delta\tau-\theta)_{90°}-\tau/2]_n;$$

means for transmitting said multi-pulse sequence at a transmit frequency offset in relation to the predetermined resonant frequency of irradiated nuclei of a prescribed substance to permeate a specimen and accommodate any intensity variation mechanisms;

means for receiving nuclear resonance echo signals issued by any nuclei within said specimen irradiated by said multi-pulse sequence;

means for analysing said received resonance echo signals and establish whether any of received resonance echo signals indicate the presence of said prescribed substance in said specimen; and means for issuing an alarm in response to said analysing means establishing that some of said received nuclear resonance echo signals indicate the presence of said prescribed substance in said specimen;

wherein said analysing involves summing all said nuclear resonance echo signals to generate a resultant signal, performing a Fourier transform on said resultant resonance signal, registering only those signals falling within a narrow band range corresponding to the resonance frequencies of irradiated nuclei of said prescribed substance in a set temperature range, and then comparing the registered signals with said set reference values corresponding to said prescribed substance to determine whether said prescribed substance is present or not in said specimen.

23. A method for detecting a prescribed substance, comprising:

irradiating nuclei of a specimen in which the prescribed substance is sought to be detected using a pulse sequence $[\tau/2-(\theta-\Delta\tau-\theta)_{0°}-\tau-(\theta-\Delta\tau-\theta)_{90°}-\tau/2]_n$; and detecting any echo signals from the specimen and, based on the detecting, determining the presence/absence of the prescribed substance, wherein $\theta$ is a flipping angle, $\tau$ is an interval between an adjacent pair of pulses, $\Delta\tau$ is the interval between pulses within a pair of pulses and the indices 0° and 90° indicate phase.

24. The method according to claim 23, wherein the interval between the pulses within a pulse pair is less than the interval between adjacent pulse pairs.

25. The method according to claim 23, the transmit frequency of the pulse sequence is offset relative to the resonant frequency of irradiated nuclei of the prescribed substance.

26. An apparatus for detecting a prescribed substance, comprising:

a radiating element for irradiating nuclei of a specimen in which the prescribed substance is sought to be detected using a pulse sequence $[\tau/2-(\theta-\Delta\tau-\theta)_{0°}-\tau-(\theta-\Delta\tau-\theta)_{90°}-\tau/2]_n$;

a detector for detecting any echo signals from the specimen; and processing circuitry for determining the presence/absence of the prescribed substance based on the detecting, wherein $\theta$ is a flipping angle, $\tau$ is an interval between an adjacent pair of pulses, $\Delta\tau$ is the interval between pulses within a pair of pulses and the indices 0° and 90° indicate phase.

27. The apparatus according to claim 26, wherein the interval between the pulses within a pulse pair is less than the interval between adjacent pulse pairs.

28. The apparatus according to claim 26, the transmit frequency of the pulse sequence is offset relative to the resonant frequency of irradiated nuclei of the prescribed substance.

29. The apparatus according to claim 26, wherein the radiating element and the detector are incorporated in a probe.

30. An apparatus for detecting a prescribed substance, comprising:

means for irradiating nuclei of a specimen in which the prescribed substance is sought to be detected using a pulse sequence $[\tau/2-(\theta-\Delta\tau-\theta)_{0°}-\tau-(\theta-\Delta\tau-\theta)_{90°}-\tau/2]_n$;

means for detecting any echo signals from the specimen; and means for determining the presence/absence of the prescribed substance based on the detecting, wherein $\theta$ is a flipping angle, $\tau$ is an interval between an adjacent pair of pulses, $\Delta\tau$ is the interval between pulses within a pair of pulses and the indices 0° and 90° indicate phase.

* * * * *